(12) United States Patent
Vodovotz et al.

(10) Patent No.: US 6,811,965 B2
(45) Date of Patent: Nov. 2, 2004

(54) KIDNEY PERFUSION SOLUTION CONTAINING NITRIC OXIDE DONOR, INHIBITOR OF NOS2, GLUTATHIONE, GLUCONATE AND METHODS OF USE

(76) Inventors: Yoram Vodovotz, 1607 Franklin Fields Dr., Sewickley, PA (US) 15143;
Frederick A. Gage, 11104 Lund Pl., Kensington, MD (US) 20895

(*) Notice: Subject to any disclaimer, the term of this patent is extended or adjusted under 35 U.S.C. 154(b) by 71 days.

(21) Appl. No.: 10/220,133

(22) PCT Filed: Mar. 2, 2001

(86) PCT No.: PCT/US01/06631
§ 371 (c)(1),
(2), (4) Date: Aug. 28, 2002

(87) PCT Pub. No.: WO01/65935
PCT Pub. Date: Sep. 13, 2001

(65) Prior Publication Data
US 2003/0104348 A1 Jun. 5, 2003

Related U.S. Application Data
(60) Provisional application No. 60/187,884, filed on Mar. 8, 2000.

(51) Int. Cl.$^7$ ................................................ A01N 1/02
(52) U.S. Cl. ...................................................... 435/1.2
(58) Field of Search ............................ 435/1.1, 1.2, 1.3

(56) References Cited

U.S. PATENT DOCUMENTS 5,789,447 A    8/1998   Wink, Jr. et al. ............ 514/611

OTHER PUBLICATIONS

Light et al., "Immediate Function and Cost Comparison Between Ice Storage and Pulsatile Preservation in Kidney Recipients At One Hospital," 27 *Transplantation Proc.* 2962 (1995).
Klahr et al., "Renal Disease: The Two Faces of Nitric Oxide," 72 *Laboratory Inv.* 1 (1995).
Ioannididis et al.,"Evidence For Increased Nitric Oxide Production After Liver Transplantation in Humans," 59 *Transplantation* 1293 (1995).
Smith et al., "Nitric Oxide Synthase Induction With Renal Transplant Rejection Or Infection," 50 *Kidney International* 2088 (1996).
Smith et al., "Temporal Changes of Cytokines and Nitric Oxide Products In Urine From RenalTransplant Patients," 58 *Kidney International* 829 (2000).
Koyama et al., "Serum Nitric Oxide Level As A Prognostic Parameter For Chronic Rejection After Renal Transplantation," 32 *Transplantation Proc.* 1789 (2000).
Keefer et al., ""NONOates" (1–Substituted Diazen–1–ium–1,2–diolates) As Nitric Oxide Donors: Convenient Nitric Oxide Dosage Forms," 268 *Methods In Enzymology* 281 (1996).
Henry et al., "Renal Blood Flow And Intrarenal Resistance Predict Immediate Renal Allograft Function," 18 *Transplantation Proc.* 557 (1996).
Petros et al., "Effects Of A Nitric Oxide Synthase Inhibitor In Humans With Septic Shock," 28 *Cardiovascular Res.* 34 (1994).
Boudjema et al., "Changes In Glutathione Concentration In Hypothermically Perfused Dog Kidneys," 117 *J. Lab. Clin. Med.* 131 (1991).
Rodriguez et al., "Role of Sodium Nitroprusside In the Improvement of Rat Liver Preservation in University of Wisconsin Solution: A Study In the Isolated Perfused Liver Model," 87 *J.Surgical Res.* 201 (1999).
Vos et al., "Inhibition of Inducible Nitric Oxide Synthase Improves Graft Funtion and Reduces Tubulointerstitial Injury in Renal Allograft Rejection," *Eur.J. Pharmacology 391* 31 (2000).
Worrall et al., "Inhibition of Inducible Nitric Oxide Synthase Prevents Mycardial and Systemic Vascular Barrier Dysfunction During Early Cardiac Allograft Rejection," 78 *Circ. Res.* 769 (1996).
*Mashiach et al., "Renal ischemia—Reperfusion Injury: Contribution of Nitric Oxide and Renal Blood Flow," 80 *Nephron* 458 (1998).

Primary Examiner—Sandra Saucier
(74) Attorney, Agent, or Firm—James C. Lydon

(57) ABSTRACT

A kidney perfusion solution which includes at least one gluconate salt; glutathione; a nitric oxide donor chemical and a chemical inhibitor selective for the inducible isoform of the enzyme nitric oxide synthase; optionally further containing a reagent that causes the reduction of oxidized glutathione. A process for preserving a kidney for transplantation is also disclosed, which includes perfusing the kidney with an amount of a nitric oxide donor chemical in an amount sufficient to mimic enzymatic production of NO by NOS3 or NOS1, while preventing generation of an excessive amount of nitric oxide by the NOS2 isoform of nitric oxide synthase, with or without a reagent that causes the reduction of oxidized glutathione. The invention also includes a process wherein a deceased donor's body is perfused with a solution containing an NO donor, with or without a reagent that causes the reduction of oxidized glutathione, prior to removal of the organs for transplantation.

18 Claims, 9 Drawing Sheets

*: $P < 0.05$ vs. Control, baseline

KIDNEY PERFUSION SOLUTION CONTAINING NITRIC OXIDE DONOR, INHIBITOR OF NOS2, GLUTATHIONE, GLUCONATE AND METHODS OF USE

This application is a U.S. national stage of International Application PCT/US01/06631, filed Mar. 2, 2001, which claims benefit of U.S. provisional application 60/187,884, filed Mar. 8, 2000.

BACKGROUND OF THE INVENTION

This invention relates to kidney perfusion solutions and a method for increasing the viability of perfused kidneys prior to transplantation.

Kidneys must be preserved for a period of at least 5 hours prior to transplantation to obtain proper pathology assessment of the suitability of the organ for transplantation. Lack of proper preservation leads to degradation of organ function due to thrombosis (blood clotting), ischemia (lack of oxygen), or ischemia followed by reperfusion (the restoration of blood flow upon transplantation). These events bring about inflammation, cell death, and eventually failure of the organ. The preferred method for preserving kidneys is pulsatile preservation.

Pulsatile kidney preservation is a process in which the renal artery is connected to a kidney perfusion machine in order to simulate the normal process by which nutrients are supplied to the kidney. A solution is continuously perfused through a closed circuit which includes the kidney, which is typically maintained at 5 degrees C. In order for pulsatile preservation to be an effective method for preservation of "extended criteria" organs (i.e., organs which are less optimal than those currently accepted for transplantion), the technician needs to monitor closely not just perfusion pressure, flow, and vascular resistance, but also the organ's chemistries, including base excess, oxygen saturation, calcium, potassium, hematocrit, $pO_2$, pH, and bicarbonate. This method has become the standard of care for kidney transplantation, due to its efficacy and cost effectiveness. See Light et al., "Immediate function and cost comparison between static and pulsatile preservation in kidney recipients," Clin. Transplantation 233–236 (1996).

Although pulsatile perfusion of kidneys is superior to static preservation methods, pulsatile perfusion suffers from several drawbacks. It requires continuous monitoring and correction of chemistries as well as pressure and flow in order to be optimal, and thus the process is time- and labor-intensive (and hence expensive). Moreover, organ perfusion requires extensive expertise, and results can vary from perfusionist to perfusionist. Another problem that is observed with current kidney perfusion solutions is the rapid oxidation of glutathione, a key component of current kidney perfusion solutions that serves as an antioxidant. Finally, pulsatile preservation has only proven marginally effective at preserving organs from "extended criteria" donors.

Nitric oxide (NO) can have both beneficial and detrimental effects in the kidney. A low level of NO, produced by the so-called constitutive nitric oxide synthases (NOS), found in endothelial cells (NOS3; ecNOS) or neurons and some other cell types (NOS1; nNOS), appears to be necessary for the maintenance of homeostasis in the kidney. See, for example, Kone et al., "Biosynthesis and homeostatic roles of nitric oxide in the normal kidney," Am. J. Physiol. F561–578 (1997) and Radermacher et al., "Importance of NO/EDRF for glomerular and tubular function: studies in the isolated perfused rat kidney," Kidney Int. 1549–1559 (1992). However, it has also been reported that high levels of NO produced by the inducible nitric oxide synthase (NOS2) during the process of kidney damage and/or transplantation are detrimental to the kidney, Klahr et al., "Renal disease: The two faces of nitric oxide," Lab. Invest. 1–3 (1995). All three isoforms of NOS (NOS1, NOS2, and NOS3) are found in the kidney, though not all of their functions are known. See, for example, Kone et al, "Localization and regulation of nitric oxide synthase isoforms in the kidney," Semin. Nephrol. 230–241 (1999).

Transplant patients are often treated with immunosuppressive agents such as cyclosporine A in order to prevent transplant rejection. Such immunosuppressive agents can suppress nitric oxide production in the normal kidney, and thus can suppress certain kidney functions. See Bloom et al, "An experimental study of altered nitric oxide metabolism as a mechanism of cyclosporin-induced renal vasoconstriction," Br. J. Surg. 195–198 (1995) and Gaston et al., "Cyclosporine inhibits the renal response to L-arginine in human kidney transplant recipients," J. Am. Soc. Nephrol. 1426–1433 (1995).

Nitric oxide donor chemicals are known, and have proven safe and efficacious at modulating various physiological and pathological parameters associated with the presence of nitric oxide. The nitric oxide donor chemical S-nitrosoglutathione (GSNO) has been reported to reduce platelet aggregation both in vitro and in vivo, to reduce acute myocardial infarction and unstable angina, to be of therapeutic benefit to patients with the HELLP syndrome and in fetal pre-eclampsia, to inhibit platelet activity in patients undergoing percutaneous transluminal coronary angioplasty (PTCA) or saphenous vein grafts, and to inhibit vasospasm in human coronary arteries. GSNO was found to suppress thrombosis in a porcine model of balloon angioplasty and subsequent endovascular radiation, see Vodovotz et al., "S-nitrosoglutathione reduces non-occlusive thrombosis rate following balloon overstretch injury and intracoronary radiation of porcine coronary arteries," 48 Int. J. Radiat. Oncol. Biol. Phys. 1167–1174 (2000).

Sodium nitroprusside, another nitric oxide donor chemical, has recently been suggested for addition to static liver perfusion solution. Rodriguez et al., "Role of sodium nitroprusside in the improvement of rat liver preservation in University of Wisconsin solution: A study in the isolated perfused liver model," 87 J.Surg.Res. 201–208 (1999).

An object of the present invention is to preserve kidneys that have been taken from donors prior to transplantation into a recipient, by providing the low levels of nitric oxide necessary for optimal kidney function (essentially substituting for reduced levels or activity of NOS1 or NOS3), while inhibiting over-exuberant enzymatic production of NO from NOS2 that can damage the kidney.

A feature of the present invention is the presence of a nitric oxide donor chemical and a chemical inhibitor selective for the inducible isoform of nitric oxide synthase (NOS2) in a kidney pulsatile perfusion solution.

An advantage of the present invention is that it should permit the transplantation of kidneys from donors whose kidneys are less optimal than those accepted currently ("extended criteria" organs).

Use of a particular nitric oxide donor chemical, GSNO, would have an additional advantage in that it would generate oxidized glutathione in addition to nitric oxide. This oxidized glutathione, if given simultaneously with an additional reagent that could reduce glutathione back to its bioactive form (such as the enzyme glutathione reductase as well as the necessary cofactors for the activity of this enzyme) would yield higher levels of bioactive glutathione.

SUMMARY OF THE INVENTION

In one aspect, the present invention is directed to a kidney pulsatile perfusion solution comprising at least one gluconate salt, glutathione, a nitric oxide donor chemical, and a chemical inhibitor selective for the inducible isoform of nitric oxide synthase.

In another aspect, the present invention relates to an improved process for perfusing a kidney with an amount of a nitric oxide donor chemical in an amount sufficient to mimic enzymatic production of nitric oxide by the beneficial enzymes NOS1 or NOS3, while preventing generation of an excessive amount of nitric oxide by NOS2.

In a third aspect, the present invention is directed to a method for increasing the availability of bioactive glutathione in a perfusion solution by including an additional reagent to reduce glutathione back to its bioactive form.

DETAILED DESCRIPTION OF THE PREFERRED EMBODIMENTS

Figure 1:
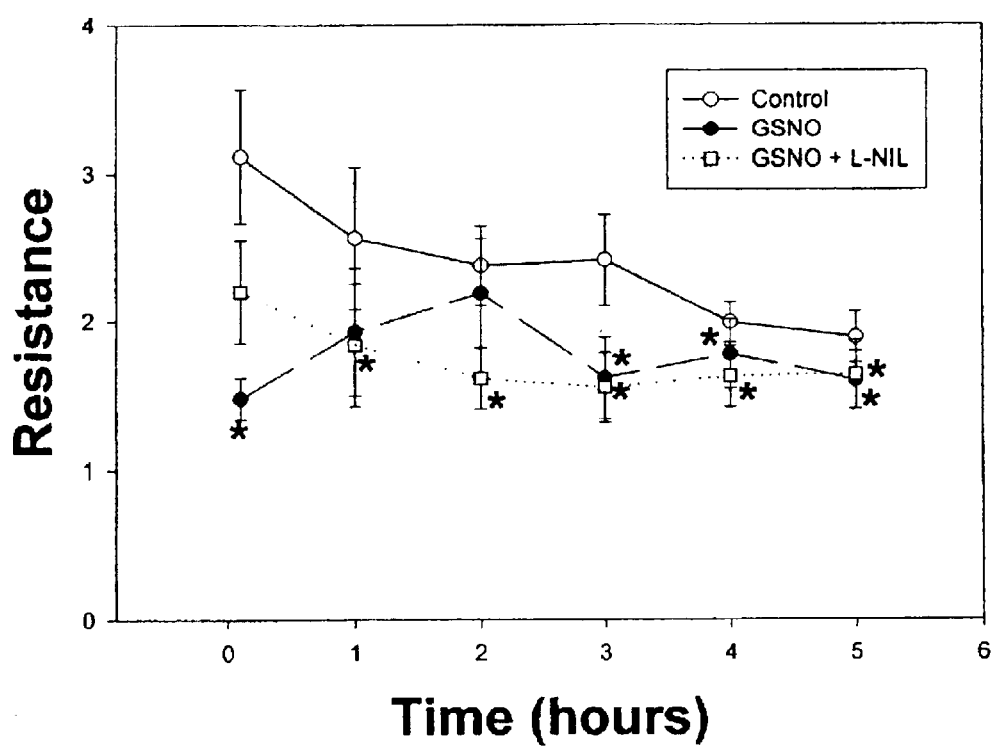
FIG. 1 is a is a plot of vascular resistance vs. time for porcine kidneys perfused with either a control perfusion solution, the control perfusion solution additionally containing a nitric oxide donor chemical S-nitrosoglutathione (GSNO), or the control perfusion solution additionally containing GSNO and N-omega-imino ethyl lysine (L-NIL), a chemical inhibitor selective for the inducible isoform of the enzyme nitric oxide synthase.
Figure 2:
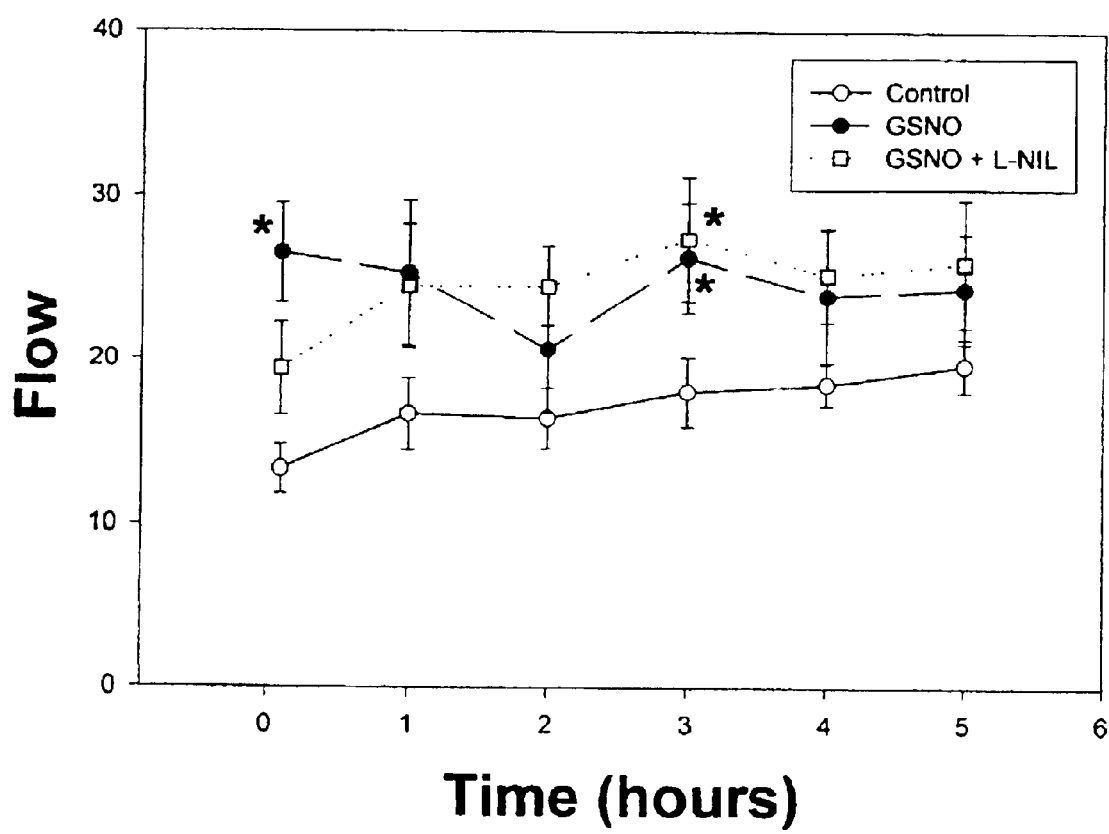
FIG. 2 is a is a plot of flow vs. time for porcine kidneys perfused with either a control perfusion solution, the control perfusion solution additionally containing GSNO, or the control perfusion solution additionally containing GSNO and L-NIL.
Figure 3:
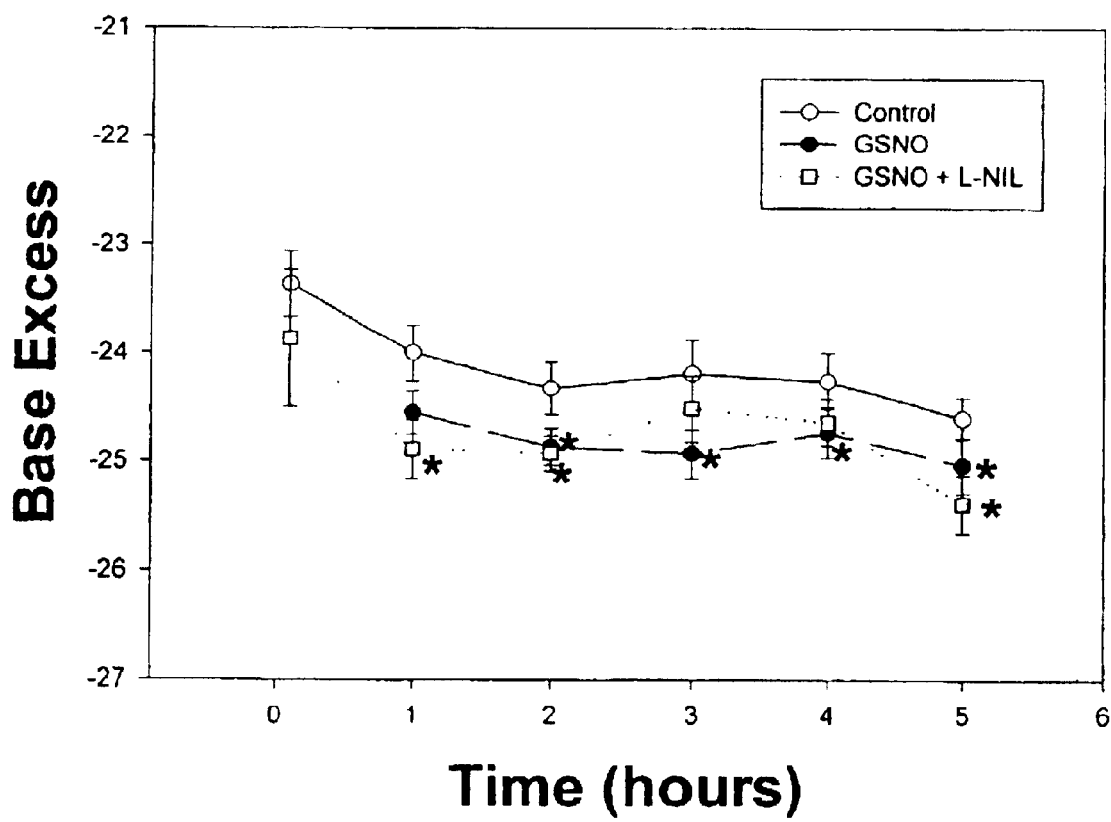
FIG. 3 is a is a plot of base excess vs. time for porcine kidneys perfused with either a control perfusion solution, the control perfusion solution additionally containing GSNO, or the control perfusion solution additionally containing GSNO and L-NIL.
Figure 4:
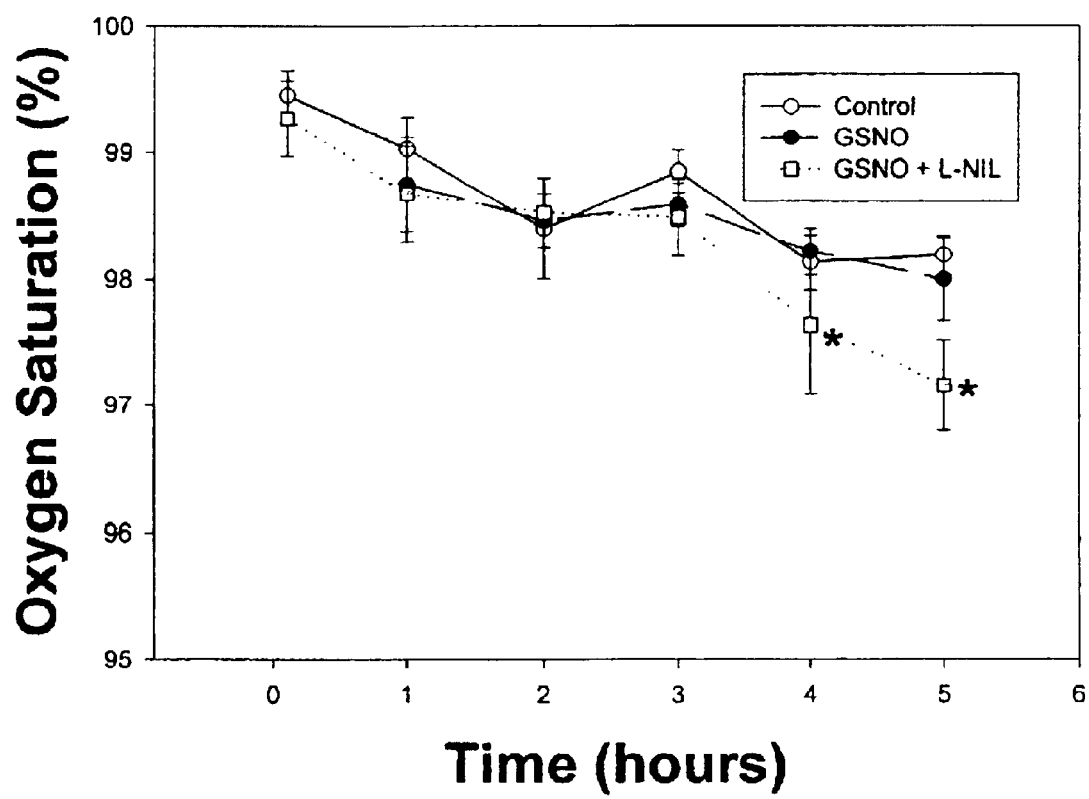
FIG. 4 is a is a plot of oxygen saturation vs. time for porcine kidneys perfused with either a control perfusion solution, the control perfusion solution additionally containing GSNO, or the control perfusion solution additionally containing GSNO and L-NIL.
Figure 5:
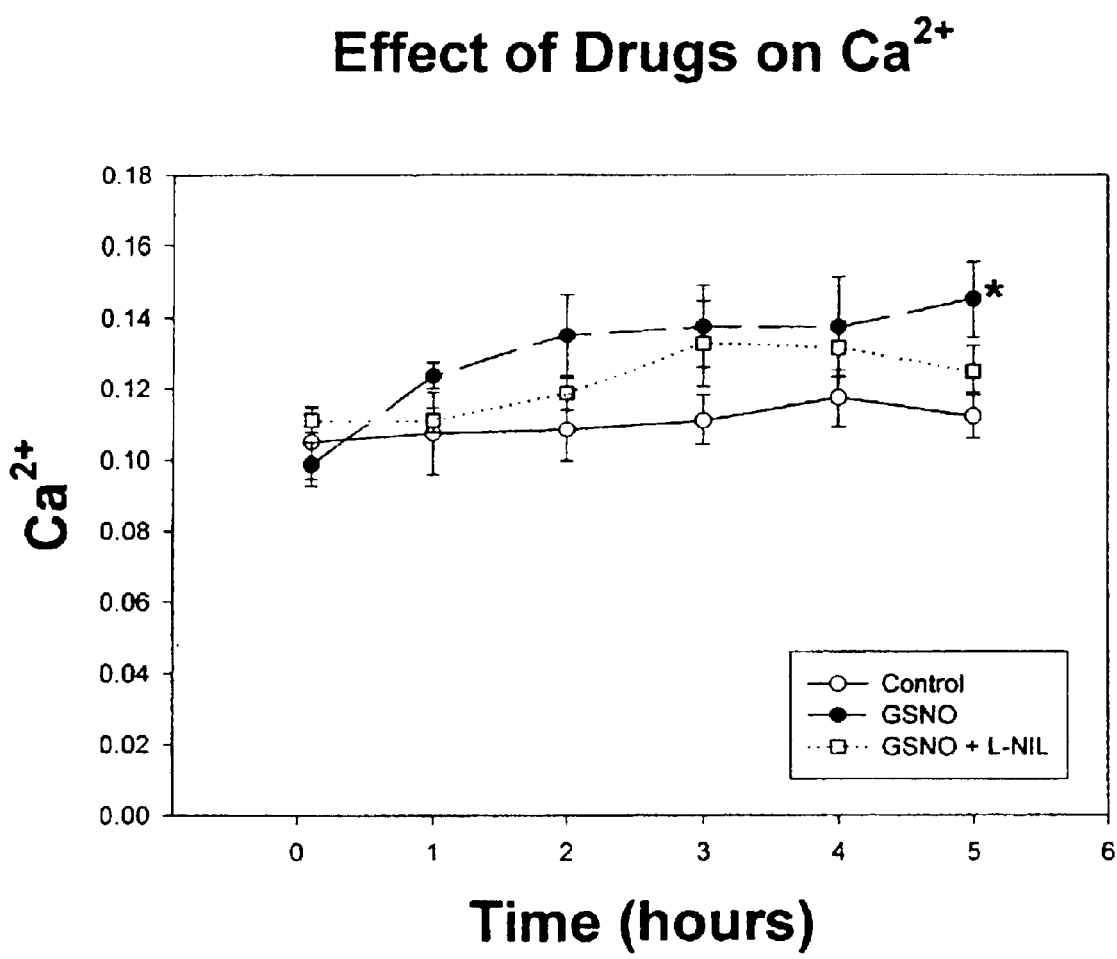
FIG. 5 is a is a plot of calcium vs. time for porcine kidneys perfused with either a control perfusion solution, the control perfusion solution additionally containing GSNO, or the control perfusion solution additionally containing GSNO and L-NIL.
Figure 6:
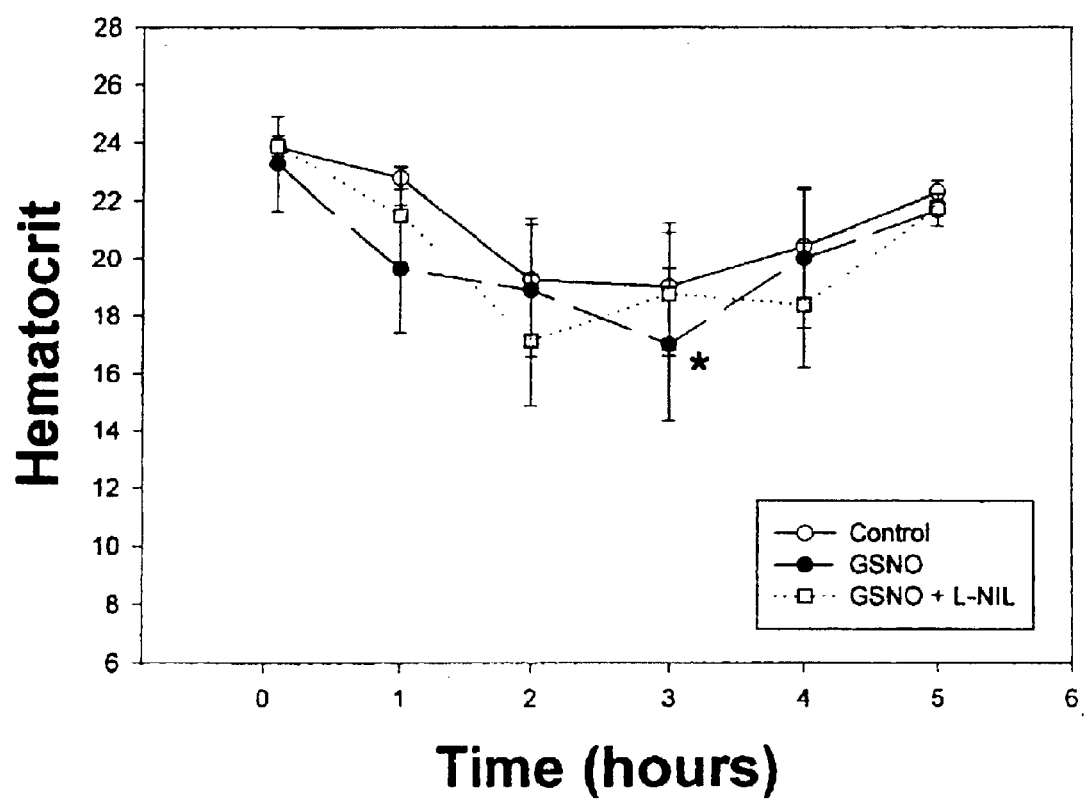
FIG. 6 is a plot of hematocrit vs. time for porcine kidneys perfused with either a control perfusion solution, the control perfusion solution additionally containing GSNO, or the control perfusion solution additionally containing GSNO and L-NIL.

A "nitric oxide donor chemical" is a chemical that can decompose into nitric oxide and a residue of the nitric oxide donor chemical, which may promptly react with one or more compounds found in the medium in which the nitric oxide chemical donor decomposes. Nitric oxide donor chemicals include, but are not limited to, S-nitrosoglutathione (molecular weight 336.3), S-nitrosoalbumin (molecular weight approximately 66,000), S-nitroso-N-acetyl-D,L-penicillamine (molecular weight 220.3), diethylamine-NONOate (1,1-Diethyl-2-hydroxy-2-nitroso-hydrazine sodium; molecular weight 155.13), diethylenetriamine-NONOate (2,2'-(Hydroxynitrosohydrazono)bis-ethanimine; molecular weight 163.18), and spermine-NONOate (N-(2-Aminoethyl)-N-(2-hydroxy-2-nitrosohydrazino)-1,2-ethylenediamine; molecular weight 262.36), and their pharmaceutically acceptable salts, esters and derivatives. Such nitric oxide chemical donors can be stored as powders for extended periods, and decompose spontaneously when placed in solution to yield nitric oxide and a nitric oxide donor chemical residue. See Keefer, L. K. et al, "'NON-Oates' (1-substituted diazen-1-ium-1,2-diolates) as nitric oxide donors: convenient nitric oxide dosage forms," *Meth-ods Enzymol.* 281–293 (1996); and Stamler, J. S., "S-nitrosothiols and the bioregulatory actions of nitrogen oxides through reactions with thiol groups," *Curr. Top. Microbiol. Immunol.* 19–36 (1995), the disclosures of which are each incorporated by reference herein in their entirety.

S-nitrosoglutathione and S-nitrosoalbumin are particularly preferred as nitric oxide donor chemicals because they decompose, either directly or indirectly, to yield NO and a residue compound, oxidized glutathione and albumin, respectively, both of which are components of conventional kidney pulsatile preservation solutions.

Any conventional kidney pulsatile perfusion solution may be employed in the present invention. Kidney pulsatile perfusion solutions typically contain the following reagents, in various proportions: sodium gluconate, hydroxyethyl starch, human serum albumin, $KH_2PO_4$, glucose, glutathione, adenosine, magnesium gluconate, adenine, ribose, calcium chloride, Hepes (N-[2-Hydroxyethyl] piperazine-N0-[2-ethanesulfonic acid]), mannitol, penicillin G, dexamethasone, and insulin. Table 1 below lists the components of an illustrative kidney perfusion solution:

TABLE 1

Kidney Perfusion Solution Formulation

| Component | Concentration Range | Preferred Concentration |
|---|---|---|
| Sodium Gluconate | 60–80 millimolar | 65–75 millimolar |
| Potassium Gluconate | 5–15 millimolar | 8–12 millimolar |
| Magnesium Gluconate | 2–9 millimolar | 4–6 millimolar |
| Hydroxyethyl Starch | 40–60 g/liter | 45–55 g/liter |
| $KH_2PO_4$ | 10–20 millimolar | 13–17 millimolar |
| Glutathione | 2–7 millimolar | 2–4 millimolar |
| Hepes | 5–15 millimolar | 8–12 millimolar |

TABLE 1-continued

Kidney Perfusion Solution Formulation

| Component | Concentration Range | Preferred Concentration |
|---|---|---|
| Adenine | 2–10 millimolar | 3–7 millimolar |
| Ribose | 2–10 millimolar | 3–7 millimolar |
| CaCl$_2$ | 0.2–0.8 millimolar | 0.4–0.6 millimolar |
| Allopurinol | 0.5–2 millimolar | 0.5–1.5 millimolar |
| Insulin | 30–50 Units/liter | 35–45 Units/liter |
| Dexamethasone | 6–10 mg/ml | 7–9 mg/ml |

The kidney perfusion solution of the present invention includes at least one nitric oxide donor chemical in an amount which is effective to preserve a kidney prior to transplantation. A preferred nitric oxide donor chemical concentration range is 10 to 500 micromolar, still more preferably 20 to 125 micromolar.

Without intending to be bound by theory, the inventors currently believe that the addition of a nitric oxide donor chemical to an otherwise conventional kidney perfusion solution will increase the bioavailability of NO, and thus enhance the viability and increase certain functions of kidneys maintained on perfusion machines in preparation for transplantation. Kidneys thus treated will have a greater chance of maintaining function in the patient after transplantation. The inclusion of a nitric oxide donor chemical in organ pulsatile perfusion solutions should therefore permit the transplantation of kidneys from donors who are more marginal than those accepted currently.

Most nitric oxide donor chemicals decompose spontaneously in the type of solutions used to perfuse kidneys, and nitric oxide donor chemicals with very different rates of decomposition are available. Proper selection of the nitric oxide donor chemical will permit appropriate control over the rate of NO produced over time ("flux"), depending on whether short-term or prolonged bioavailability of NO is desired.

In a preferred embodiment, the nitric oxide donor chemical yields both NO and an antioxidant upon decomposition, either directly or indirectly. These antioxidants will also increase the viability and function of kidneys maintained on perfusion machines in preparation for transplantation. More particularly, the antioxidant will scavenge oxidized free radicals, which are known to cause organ damage. Thus, a particularly preferred nitric oxide chemical donor is S-nitrosoglutathione (GSNO), which will decompose to yield NO and oxidized glutathione; oxidized glutathione will then be reduced by an enzyme either present in the kidney [glutathione reductase; see Di Ilio et al., "Glutathione peroxidase and glutathione reductase activities in cancerous and non-cancerous human kidney tissues," *Cancer Lett.* 19–23 (1995)] or by the addition of glutathione peroxidase to the perfusion solution. Glutathione has been reported to have beneficial effects in isolated perfused kidneys or in ischemic kidneys. See McCoy et al., "Oxidant stress following renal ischemia: Changes in the glutathione redox ratio," *Kidney Int.* 812–817 (1988) and Boudjema et al., "Changes in glutathione concentration in hypothermically perfused dog kidneys," *J. Lab. Clin. Med.* 131–137 (1991). As described above, glutathione is used as a conventional component of current formulations of kidney pulsatile perfusion solutions. Addition of a reagent that could reduce glutathione back to its bioactive form (e.g. glutathione reductase and its requisite cofactors) would serve to increase bioactive glutathione both as a byproduct of decomposition of S-nitrosoglutathione but also from the glutathione already present in the pulsatile perfusion solution.

The kidney pulsatile solution may also contain a potent antioxidant to scavenge superoxide radical or an inhibitor which suppresses superoxide production, since superoxide can react with nitric oxide and thereby reduce the bioavailability of nitric oxide. Copper, zinc superoxide dismutase and manganese superoxide dismutase are illustrative superoxide scavengers, while ethinylestradiol may be cited as a superoxide inhibitor.

The kidney pulsatile solution of the present invention also contains a chemical inhibitor selective for the inducible isoform of the enzyme nitric oxide synthase (NOS2; iNOS). Illustrative nitric oxide synthase inhibitors include but are not limited to N-omega-imino ethyl lysine (L-NIL; molecular weight 187.2), N-omega-imino ethyl-L-ornithine (L-NIO,; molecular weight 173.2), ([aminomethyl] benzyl) acetamidine (1400 W; molecular weight 177.3), S-(2-aminoethyl)-isothiourea (AET; molecular weight 119.2), aminoguanidine hydrochloride (molecular weight 74.1), S-ethyl-isothiourea (SEITU; molecular weight 104.2), and S-methyl-isothiourea (SMT; molecular weight 180.3), and their pharmaceutically acceptable salts, esters and derivatives.

The nitric oxide synthase inhibitor should be present in an amount that is effective to ensure that a harmful excess of NO is not generated during perfusion. A preferred concentration range is 10 to 5,000 micromolar. A still more preferred range is 500 to 2000 micromolar.

Again without intending to be bound by theory, the inventors currently believe that addition of a selective nitric oxide synthase inhibitor will reduce transplant rejection because induction of NOS2 in transplanted organs such as the liver has been shown to correlate with transplant rejection. See Ioannidis et al., "Evidence for increased nitric oxide production after liver transplantation in humans," *Transplantation* 1293–1297 (1995). Furthermore, the NOS2 inhibitor should improve kidney function by reducing damage to the kidneys mediated by over-exuberant production of NO (see, for example, Klahr et al., "Renal disease: The two faces of nitric oxide," *Lab. Invest.* 1–3 [1995]).

The nitric oxide donor chemical and the chemical NOS2 inhibitor, with or without an additional reagent that could reduce glutathione back to its bioactive form and thereby increase bioactive glutathione, may be added to a conventional kidney perfusion solution as a powder or liquid using conventional mixing techniques and apparatus. These additives may be added to the kidney perfusion solution just prior to starting perfusion, or alternatively, may be added earlier and the resulting solution stored prior to perfusion.

The present invention also relates to a process for preserving a kidney for transplantation by perfusing the kidney with an amount of a nitric oxide donor chemical in an amount sufficient to mimic enzymatic production of nitric oxide by NOS3 or NOS1, while preventing the generation of an excessive amount of nitric oxide by NOS2. This process may occur with or without an additional reagent that could reduce glutathione back to its bioactive form in order to increase bioactive glutathione. The organ to be transplanted may be perfused initially with a conventional static perfusion and then placed on a pulsatile perfusion circuit with a solution containing a nitric oxide donor chemical and the chemical NOS2 inhibitor, with or without an additional reagent that could reduce glutathione back to its bioactive form to increase bioactive glutathione. Alternatively, the initial static perfusion may be performed with a solution containing a nitric oxide donor chemical and the chemical NOS2 inhibitor, with or without an additional reagent that could reduce glutathione back to its bioactive form to increase bioactive glutathione. Thus, the present invention relates to a process for preserving a kidney that includes the following steps:

1. Flushing a kidney with a conventional flushing solution or with a flushing solution that contains a nitric oxide chemical donor and a chemical inhibitor of NOS2 (with or without an additional reagent that could reduce glutathione back to its bioactive form) at a temperature of below 10 degrees C.;
2. Placing a cannula in the perfused kidney and mounting it in a pulsatile perfusion cassette, connected to a pulsatile perfusion apparatus;
3. Perfusing the kidney with a pulsatile perfusion solution that contains a nitric oxide chemical donor and a chemical inhibitor of NOS2 (with or without an additional reagent that could reduce glutathione back to its bioactive form) for up to 8 hours at a temperature of below 10 degrees C.;
4. Monitoring at least one physiological parameter which is indicative of organ function, including but not limited to: perfusion pressure, flow, vascular resistance, base excess, oxygen saturation, calcium, potassium, hematocrit, $pO_2$, pH, and bicarbonate.

The kidney is preferably maintained on a pulsatile preservation system at approximately 5 degrees C. until the time of transplant. However, the kidney may also be perfused at room temperature.

Another aspect of this invention involves the use of chemical NO donors to maintain the function of organs while still in the deceased donor's body. In order to successfully recover organs from non-heartbeating donors (NHBD), from whom organs are recovered after the heart has stopped beating and all resuscitation methods have failed, the trauma caused by ischemia or ischemia followed by reperfusion must be addressed. Herein, it is proposed to address this problem by supplementing with NO the flush solution used to initially perfuse these organs. In order to accomplish this successfully, the following procedure may be followed:

a) After death has been declared, the donor is aseptically prepared for surgery, scrubbed and painted.
b) A femoral cut down is initiated, finding and isolating both the femoral artery and vein in either the left or right groin depending on the physician's preference.
c) The femoral artery is then cannulated with a 16 fr catheter, Porges MOP, and the femoral vein is cannulated with a 26 through 34fr venous return cardiothoracic vascular catheter.
d) The Porges catheter is primed with Lactated Ringer's solution (containing NaCl, sodium lactate, $CaCl_2$, and KCl in distilled water) or Plasmanate® solution (Plasma Protein Fraction [Human] 5%, USP; contains 5 g selected plasma proteins [88% normal human albumin, 12% alpha and beta globulins and not more than 1% gamma globulin] buffered with sodium carbonate and stabilized with 0.004 M sodium caprylate and 0.004 M acetyltryptophan) at room temperature (25 degrees C.), removing air, and the solution is circulated through the vascular system of the donor to flush out the donor's non-oxygenated blood.
e) Once the donor's blood has been drained out, the drainage circuit is then closed off and then a solution of Lactated Ringer's will have nitric oxide, in the form of one or more of the chemical nitric oxide donors mentioned above, added to the flush solution along with oxygen.

The donor will be perfused with this solution for a minimum of 30 minutes, at which point the solution will be cooled down to a temperature below 10 degrees C. The solution will continue to be perfused through the circuit until the donor is ready for the surgeon to remove the organs.

EXAMPLES

The following Examples illustrate in even greater detail specific embodiments of the invention. These Examples are intended to illustrate the practice and advantages of the invention, and are not intended to limit the allowable scope of the invention in any manner whatsoever.

Example 1

Preparation of a Kidney Perfusion Solution Containing A Nitric Oxide Donor Chemical And A Chemical NOS2 Inhibitor GSNO and L-NIL dihydrate hydrochloride were purchased from Alexis Corporation (San Diego, Calif.). Solution A was prepared by weighing out 30 milligrams of GSNO powder and adding it to 1 milliliter of Belzer Machine Perfusion solution (Transmed, Elk Grove, Minn.), and then injecting it into 1 liter of Belzer Perfusion solution while the perfusion solution was circulating through a Waters Instruments (Rochester, Minn.) kidney perfusion circuit (final concentration: 30 milligrams/liters; 90 micromolar). Solution B was prepared by weighing out 187 milligrams of L-NIL dihydrate hydrochloride powder and adding it to 3.5 milliliters of Belzer Machine Perfusion solution, and then injecting it into Solution A while the solution was circulating through a Waters Instruments kidney perfusion circuit (final concentration: 187 milligrams/liter; 694 micromolar).

Example 2

Preservation of Porcine Kidneys Using Pulsatile Perfusion Solutions

Porcine kidneys were obtained following a warm ischemic time of 30–45 minutes. The kidneys were flushed with 1 L of Lactated Ringer's solution at 5 degrees C., and then flushed with 1 L Viaspan™ solution (DuPont, Wilmington, Del.) at 5 degrees C. The kidneys were then stored at 5 degrees C. for 3–30 h, at which time the kidneys were placed on a Waters Instruments (Rochester, Minn.) kidney perfusion circuit and perfused with 1 L of Belzer Machine Perfusion solution (Transmed, Elk Grove, Minn.). During the perfusion period, the kidneys were kept at a constant pressure of 40 mmHg. Eight kidneys were perfused with Belzer Machine Perfusion solution only, another eight kidneys were perfused with Belzer Machine Perfusion solution containing solution A (prepared as in Example 1), and a further eight kidneys were perfused with Belzer Machine Perfusion solution containing Solution B (prepared as in Example 1).

Hourly samples (3 ml total) were taken from each kidney for at least 5 hours, and in some cases 6 hours. Blood chemistry was analyzed using a GEMStat analyzer (Instruments Laboratory, Boston, Mass.). Statistical analyses were performed using Sigmastat software (SPSS, Chicago, Ill.).

Figure 7:
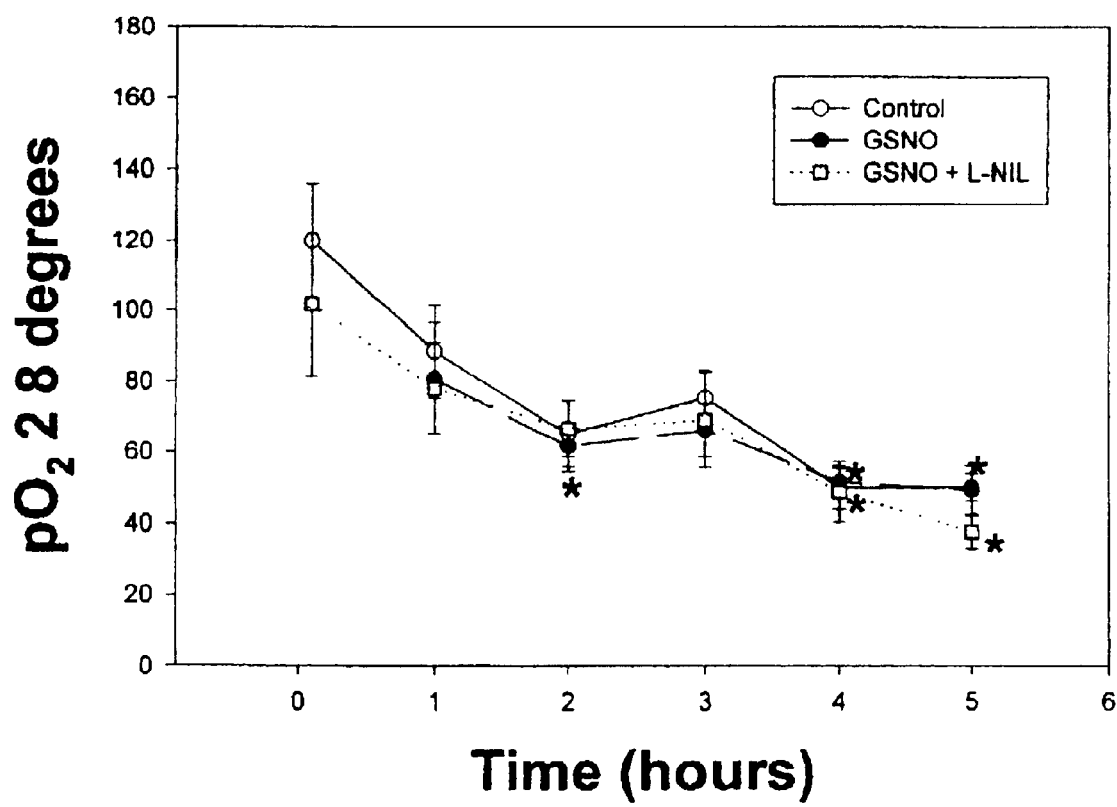
FIG. 7 is a is a plot of $pO_2$ @ 8° C. vs. time for porcine kidneys perfused with either a control perfusion solution, the control perfusion solution additionally containing GSNO, or the control perfusion solution additionally containing GSNO and L-NIL.
Figure 8:
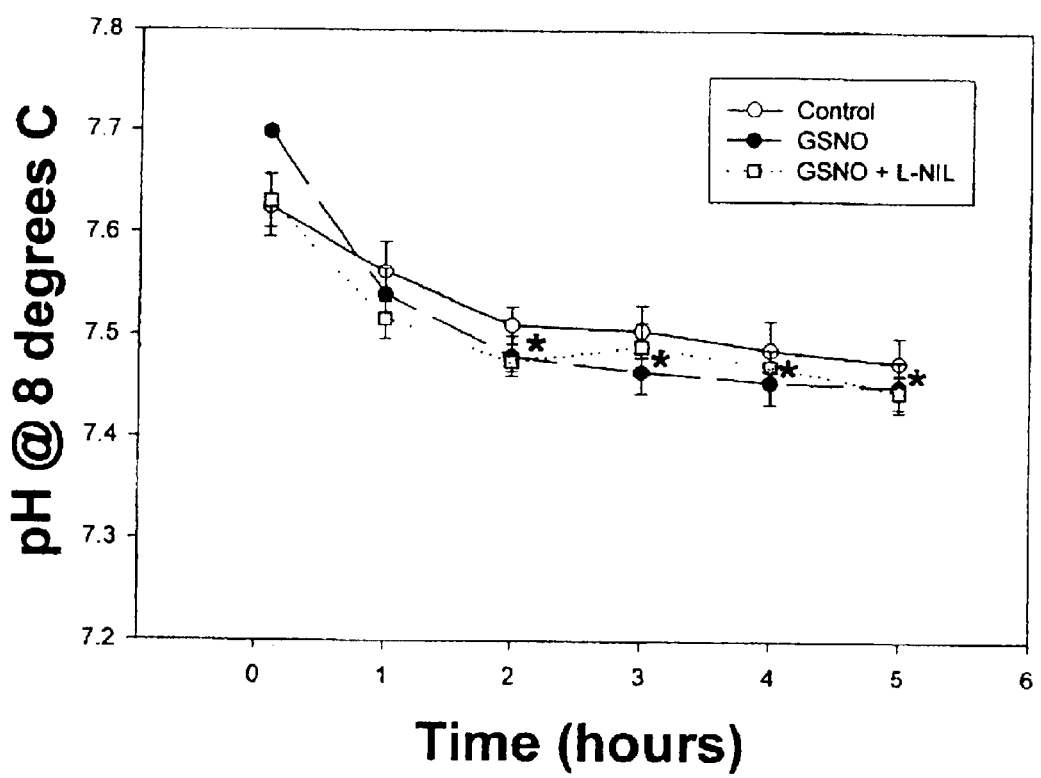
FIG. 8 is a plot of pH @ 8° C. vs. time for porcine kidneys perfused with either a control perfusion solution, the control perfusion solution additionally containing GSNO, or the control perfusion solution additionally containing GSNO and L-NIL.
Figure 9:
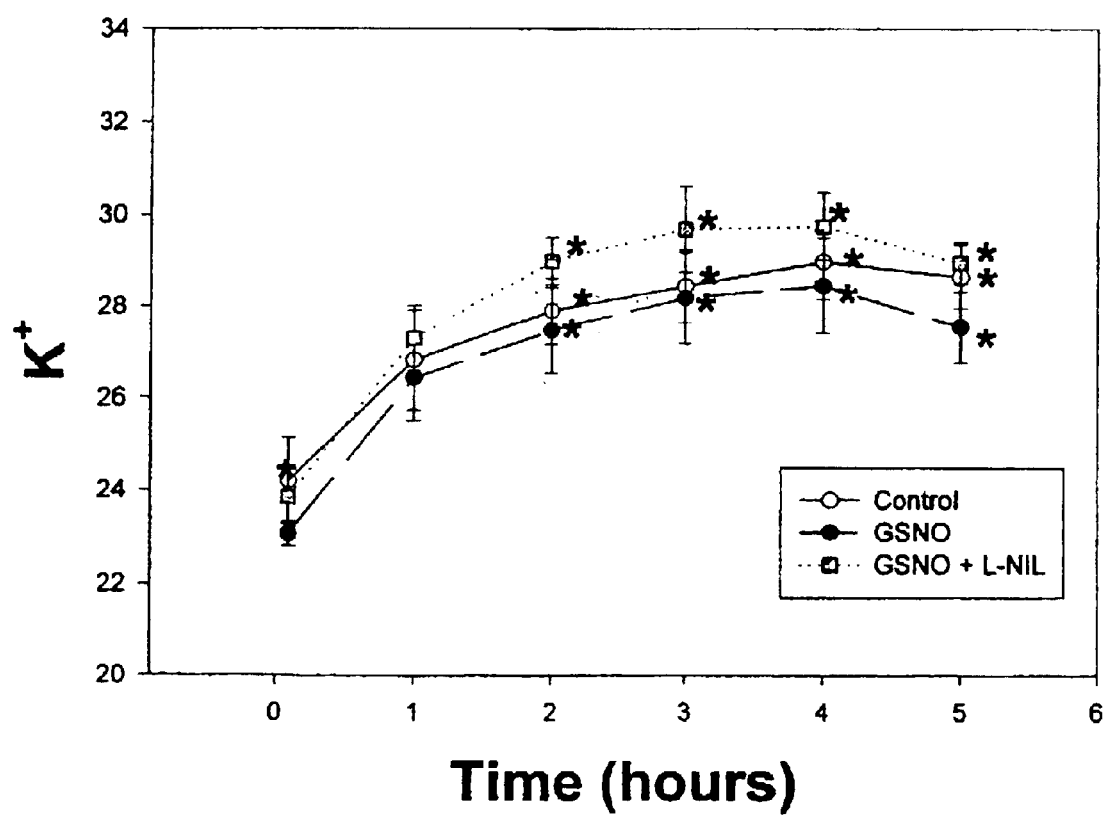
FIG. 9 is a plot of potassium vs. time for porcine kidneys perfused with either a control perfusion solution, the control perfusion solution additionally containing GSNO, or the control perfusion solution additionally containing GSNO and L-NIL.

FIGS. 1–6 show how vascular resistance, flow, base excess, oxygen saturation, calcium and hematocrit were affected by the additional presence of a nitric oxide donor chemical (GSNO) or the combination of GSNO and N-omega-imino ethyl lysine (L-NIL), a chemical inhibitor selective for the inducible isoform of the enzyme nitric oxide synthase. The greatest degree of improvement occurred with the combination of GSNO +L-NIL (Solution B). Several other parameters ($pO_2$, pH, potassium, bicarbonate and total $CO_2$) were not affected by the addition of GSNO and L-NIL. FIGS. 7–9 illustrate three of these parameters.

TABLE 2

Summary of the statistically significant effects of GSNO, with or without L-NIL on explanted kidneys, relative to control

| Treatment | Vascular Resistance | Flow | Base Excess | Oxygen Saturation | $Ca^{2+}$ | Hematocrit |
|---|---|---|---|---|---|---|
| GSNO | Lower | Higher | More negative | Equal | Higher | Lower |
| GSNO + L-NIL | Lower | Higher | More Negative | Lower | Higher (trend) | Lower (trend) |

These changes are considered beneficial for explanted organ function. For example, lower vascular resistance and higher flow indicate that a better supply of oxygen and nutrients can be provided to the explanted organ. Lower oxygen saturation indicates that the organ has been more metabolic during the pulsatile perfusion procedure, and therefore that this organ is more viable.

The treatment with GSNO and L-NIL appears to result in improved kidney function compared to GSNO alone since oxygen saturation, which is indicative of metabolic activity of the kidney, was lower in this group relative to the control kidneys. In contrast, kidneys perfused with solution A (GSNO only) did not differ statistically from the control kidneys.

Decreased vascular resistance is an indication of improved organ function. In this regard, L-NIL would be expected to increase vascular resistance by inhibiting the production of high levels of nitric oxide from NOS2 [see, for example, Petros et al., "Effects of a nitric oxide synthase inhibitor in humans with septic shock," 28 *Cardiovasc.Res.* 34–39 (1994)]. Thus, the observed decrease in vascular resistance is an unexpected and surprising result.

We claim:

1. A kidney perfusion solution comprising
   a) at least one gluconate salt;
   b) glutathione;
   c) a nitric oxide donor chemical; and
   d) a chemical inhibitor selective for the inducible isoform of the enzyme nitric oxide synthase NOS2.

2. The kidney perfusion solution of claim 1, wherein said nitric oxide donor chemical is at least one compound selected from the group consisting of S-nitrosoglutathione nitrosoalbumin; S-nitroso-N-acetyl-D, L-penicillamine 1, 1-Diethyl-2-hydroxy-2-nitroso-hydrazine sodium; 2,2'-(Hydroxynitrosohydrazono) bis-ethanimine N-(2-Aminoethyl)-N- (2-hydroxy-2-nitrosihydrazino)-1, 2-ethylenediamine and their pharmaceutically acceptable salts, esters and derivatives.

3. The kidney perfusion solution of claim 2, wherein said nitric oxide donor chemical is either S-nitrosoglutathione or S-nitrosoalbumin.

4. The kidney perfusion solution of claim 1, wherein said nitric oxide donor chemical is present in an amount of 50 to 500 micromolar.

5. The kidney perfusion solution of claim 4, wherein said nitric oxide donor chemical is present in an amount of 20 to 125 micromolar.

6. The kidney perfusion solution of claim 1, wherein said chemical inhibitor is at least one member of the group consisting of N-omega-imino ethyl lysine, N-omega-imino ethyl-L-ornithine, ([aminomethyl]benzyl) acetamidine, S-(2-aminoethyl)-isothiourea, aminoguanidine hydrochloride, S-ethyl-isothiourea, S-methyl-isothiourea and their pharmaceutically acceptable salts, esters and derivatives.

7. The kidney perfusion solution of claim 1, wherein said chemical inhibitor is present in an amount of 10 to 5000 micromolar.

8. The kidney perfusion solution of claim 7, wherein said chemical inhibitor is present in an amount of from 500 to 2000 micromolar.

9. The kidney perfusion solution of claim 1, further comprising at least one superoxide scavenger or superoxide inhibitor.

10. The kidney perfusion solution of claim 1, further comprising a reagent capable of reducing oxidized glutathione.

11. The kidney perfusion solution of claim 10, wherein said reagent comprises glutathione reductase.

12. A process for preserving a kidney, comprising:
   (a) flushing a kidney with a conventional flushing solution or with a flushing solution that contains a nitric oxide chemical donor and a chemical inhibitor of NOS2,
   (b) placing a cannula in the perfused kidney and mounting it in a pulsatile perfusion cassette, connected to a pulsatile perfusion apparatus,
   (c) perfusing the kidney with the perfusion solution of claim 1,
   (d) monitoring at lease one physiological parameter which is indicative of kidney function.

13. The process of claim 12, wherein said flushing solution further comprises an additional reagent capable of reducing oxidized glutathione back to its bioactive form.

14. The process of claim 12, wherein said flushing step is performed at a temperature of below 10 degrees C.

15. The process of claim 12, wherein said perfusion solution further comprises an additional reagent capable of reducing oxidized glutathione back to its bioactive form.

16. The process of claim 12, wherein said perfusing step is performed for up to 8 hours at a temperature of below 10 degrees C.

17. The process of claim 12, wherein said physiological parameter is a member selected from the group consisting of perfusion pressure, flow, vascular resistance, base excess, oxygen saturation, calcium, potassium, hematocrit, pO2, pH, and bicarbonate.

18. A process for maintaining the functions of organs in a cadaver, comprising,
   A. isolating both the femoral artery and vein in either the left or right groin of a cadaver;
   B. creating a flush circuit by cannulating the femoral artery with a catheter and cannulating the femoral vein with a venous return cardiothoracic vascular catheter, thereby creating a drainage circuit which includes the vascular system of the cadaver,
   C. flushing a solution through the drainage circuit until the cadaver's non-oxygenated blood has been removed from the cadaver;
   D. circulating the perfusion solution of claim 1 through said drainage system for at least 30 minutes, and
   E. circulating said perfusion solution at a temperature below 10 degrees C. through said drainage system until at least one organ is removed from said cadaver.

* * * * *